United States Patent [19]

Augustine et al.

[11] Patent Number: 4,662,870
[45] Date of Patent: May 5, 1987

[54] NEEDLE PENETRATION INDICATOR AND GUIDE

[76] Inventors: Scott D. Augustine, 4761 Olive St., San Diego, Calif. 92105; Douglas J. Augustine, Box 37, Sandstone, Minn. 55072

[21] Appl. No.: 755,169

[22] Filed: Jul. 15, 1985

[51] Int. Cl.⁴ ............................................. A61M 5/00
[52] U.S. Cl. ...................................... 604/117; 604/164
[58] Field of Search ............... 604/117, 118, 168, 170, 604/53, 158–164, 900; 128/763, 748, 771

[56] References Cited

U.S. PATENT DOCUMENTS

| | | | |
|---|---|---|---|
| 1,527,291 | 2/1925 | Zorraquin | 604/158 |
| 2,524,713 | 10/1950 | Plechas | 128/214 |
| 2,705,949 | 4/1955 | Silverman | 604/117 |
| 3,057,351 | 10/1962 | Kimura et al. | 128/218 |
| 3,185,151 | 5/1965 | Czorny | 604/163 |
| 3,903,885 | 9/1975 | Fuchs | 604/158 |
| 3,920,013 | 11/1975 | Bodzin | 604/158 |
| 4,037,600 | 7/1977 | Poncy et al. | 604/160 |
| 4,068,659 | 1/1978 | Moorehead | 604/159 |
| 4,068,660 | 1/1978 | Beck | 604/158 |
| 4,186,750 | 2/1980 | Patel | 128/748 |
| 4,207,870 | 6/1980 | Eldridge | 128/766 |
| 4,215,699 | 8/1980 | Patel | 128/748 |
| 4,356,826 | 11/1982 | Kubota | 128/630 |
| 4,414,983 | 11/1983 | Evans et al. | 128/747 |
| 4,417,886 | 11/1983 | Frankhouser et al. | 604/170 |
| 4,525,157 | 6/1985 | Vaillancart | 604/168 |
| 4,529,399 | 7/1985 | Groshong et al. | 604/159 |

*Primary Examiner*—C. Fred Rosenbaum
*Assistant Examiner*—Jerome R. Smith, Jr.
*Attorney, Agent, or Firm*—Brown, Martin, Haller & Meador

[57] ABSTRACT

A device for indicating the penetration of a needle into a vein, artery, lumen, or other cavity in a patient's body includes a filament that is moved through the needle toward its sharpened end. As the needle is inserted through bodily tissue, the distal end of the filament is retained by the tissue at the needle's sharpened end. The filament is loaded with compressive force so that the distal tip is moved through the end of the needle when the end enters a space. Penetration is indicated by the sudden movement of a visible indicator attached to the filament that is caused when the retention of the filament's distal tip is released by the penetration of the needle's end into the space.

15 Claims, 4 Drawing Figures

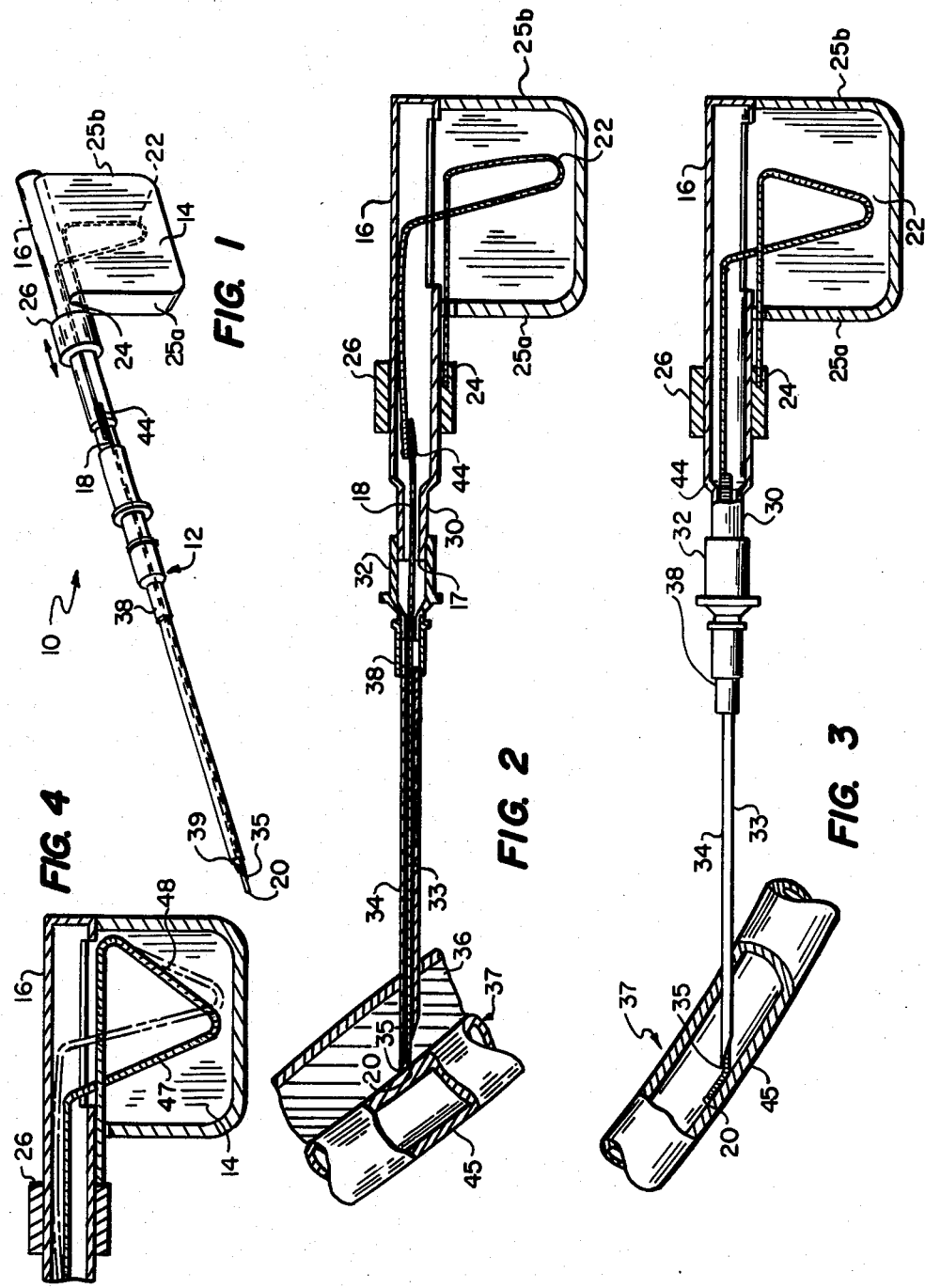

NEEDLE PENETRATION INDICATOR AND GUIDE

BACKGROUND OF THE INVENTION

The present invention relates to devices for indicating when the sharpened end of a needle has penetrated through bodily tissue into a lumen or other bodily cavity.

Certain medical procedures require the penetration of veins, arteries, or other bodily lumens by needled catheters. For example, drawing blood requires that a needle be stabbed into an artery or vein to provide a guide for insertion of a catheter which functions as a channel for the evacuation of blood. During a tracheotomy, a hollow needle is stabbed into the trachea to afford a channel and entry for a catheter, which opens a free passage for breathing.

It can be difficult to correctly determine the location of the end of the needle that is being inserted through bodily tissue into a cavity. When a blood vessel is being punctured, it is sometimes possible to detect proper penetration of the vessel by the presence of blood, if the hydraulic pressure in the vessel is sufficient to move blood through the needle. However, this may not work in the case of a vein where the fluid pressure is lower than in an artery. Of course there is no movement of fluid to signal the successful insertion of a needle into a trachea.

As is known, if there is no reliable indication of penetration, it is possible for a vessel or a lumen to be completely transfixed, with a needle passing completely through both walls of a vessel without giving any indication of having travelled through it. Complete transfixation most often happens in small vessels or in vessels whose walls flatten under pressure from a needle. In such cases, before it penetrates the near vessel wall, a needle will force the near wall against the far wall; if penetration occurs suddenly, the momentum of the needle can carry it through both the near and the (now near) far wall.

It would therefore be desirable to provide an instrument and a technique for indicating to a nurse, medical technician, or physician when the sharpened end of a needle has penetrated one wall and entered the interior of a lumen, with the indication being given quickly enough to prevent the end being pushed completely through the lumen. It would also be desirable for such an instrument to reduce the likelihood of completely transfixing a vessel by blocking the sharpened end from the back wall of the vessel once the vessel's front wall is penetrated.

SUMMARY OF THE INVENTION

The invention contemplates an apparatus for inserting the sharpened end of a hollow needle through bodily tissue into an interior lumen and indicating when the end has entered the lumen. The indication is visual and signals the user of the apparatus to stop the insertion pressure so that the needle will not be pushed entirely through the cavity. Further, when the needle end penetrates a cavity, the apparatus blocks the end of the needle from being pushed through the lumen back wall.

The penetration indicator and guide of the invention includes a housing that provides a surface to grasp for applying pressure to insert a catheter through bodily tissue. An extension of the housing provides for mounting a needle onto the housing in a position for being inserted through bodily tissue. A flexible resilient filament with a highly flexible distal tip is moveably disposed in the housing extension. The filament is attached to a collar that is slidably mounted on the housing extension. A needle with a sharpened, bevelled end is mounted to the housing for insertion through body tissue, moving the filament through the housing extension into the needle to load the distal tip against the bodily tissue being penetrated by the sharpened end. The distal tip of the filament is retained in the end of the needle by the bodily tissue during insertion through the tissue until it is moved through and beyond the tissue. When the end penetrates the near wall of the cavity in the bodily tissue, the filament is released. A visual indicator is moveably connected to the filament for indicating when the filament's distal tip moves through the needle's end into the cavity.

When the sharpened end of the needle enters the cavity, and the filament distal tip moves through the end, the flexibility of the tip will cause it to bend to the contour of the surface of the far wall of the cavity. The portion of the tip which extends beyond the end of the needle blocks the needle from penetrating the cavity's far wall.

It is therefore an object of the invention to provide a visual indication when the sharpened end of a needle enters a bodily cavity, as well as to physically block further penetration.

An advantage of such an indication is that a user of the needle penetration indicator will respond to the indication by stopping further insertion of the needle, which will prevent carrying the needle completely through the cavity.

A further object of the invention is to prevent the complete transfixation of a bodily cavity by a needle being inserted into the cavity.

Other objects and attendant advantages of this needle penetration indicator and guide will become more evident when its detailed description is read in light of the below-described drawings.

BRIEF DESCRIPTION OF THE DRAWINGS

FIG. 1 is a perspective view of the apparatus of the invention with a mounted needle and catheter assembly.

FIG. 2 is a partial cross-sectional view of the apparatus and the mounted needle showing the arrangement of parts that move a filament within the apparatus to the sharpened end of the needle before it penetrates an interior vessel.

FIG. 3 illustrates how movement of the filament indicates penetration of the vessel wall by the end of the needle.

FIG. 4 illustrates the arrangement of parts in the apparatus when the filament is retracted from the end of the needle.

DETAILED DESCRIPTION OF THE PREFERRED EMBODIMENT

In FIGS. 1 and 2 there is illustrated a needle penetration indicator and guide that provides a visible signal when the sharpened end of a needle and catheter assembly 12 penetrates into a bodily cavity such as a blood vessel. The needle penetration indicator 10 includes a housing 14 and an elongate tubular extension 16 that is attached to the housing. Preferably, the tubular extension 16 is formed from a transparent material such as a clear plastic tube. A movable filament 18 extends from the rear portion of the tube 16 through the end 17 of the tube. One end of the filament 18 has a distal tip 20 that extends beyond the end of and outside the tube 16. The other end of the filament is formed into a substantially triangular loop 22 so that the other tip 24 of the filament is doubled back to point in the same direction as the distal tip 20.

The tip 24 of the filament extends outside the housing 14 and is attached to a collar 26 that encircles the tubular extension 16. The collar 26 is longitudinally slidable on the outer surface of the tubular extension 16 toward and away from the housing 14.

The loop 22 of the filament extends downwardly from the tubular extension 16 into the hollow interior of the housing 14. The end walls 25a and b of the housing 143 constrain the loop 22 to move within the housing in a direction that is parallel to the tubular extension 16.

The filament 18 is preferably formed from a small-diameter, lightweight elongated filament of metal such as stainless steel. Preferably, the filament is tightly coiled to maximize its flexibility and resilience; this permits the filament to be flexed or bent many times without losing its ability to spring back to its original elongated shape. Further, the distal tip 20 is constructed to be more flexible than the rest of the filament 18. This permits the tip to be easily flexed to conform to the interior surface of a body cavity.

The operation of the catheter penetration indicator is illustrated in FIGS. 2-4. The conventional hollow needle and catheter assembly 12 is mounted to the penetration indicator 10 by inserting the reduced-diameter end 30 of the tubular extension 16 into the expanded-diameter socket 32 of a needle 33 forming a part of the needle and catheter assembly 12. As is conventional, the socket 32 transitions to a hollow stainless steel needle tube 34 having a sharpened, bevelled end 35. When the assembly 12 is mounted on the penetration indicator 10 as illustrated in FIGS. 1-3, it is ready to be inserted through bodily tissue 36 into an interior bodily cavity such as the blood vessel 37. This is done by stabbing the sharpened end 35 through the tissue until it penetrates the interior cavity.

The needle and catheter assembly 12 also includes a catheter 38 slidably mounted on the needle tube 34. The assembly 12 is conventionally used for penetration in the following manner: the needle is inserted through bodily tissue into a cavity; when the needle is in the cavity, the catheter is slid toward the cavity along the tube 34 until the end 39 of the catheter enters the cavity; then, the needle is backed out of the cavity and catheter with the catheter left in place to provide a channel into the cavity.

When the needle is first stabbed into the tissue 36, the sliding collar 26 is moved forward along the tubular extension 16 in the direction of the reduced diameter end 30. This causes the filament 18 to move through the tubular extension 16 and enter the needle tube 34. The filament is designed to be of such a length that movement of the sliding collar 26 to a position midway between the housing 22 and the reduced-diameter end 30 of the tubular extension will move the distal tip 20 of the filament through the needle tube 34 to a point where it protrudes slightly out of the sharpened end 35.

Then, as the end 35 is stabbed into the bodily tissue 36 toward the cavity, the sliding collar 26 is moved further toward the reduced-diameter end 30. Now, instead of sliding further beyond the sharpened end 35, the distal tip 20 of the filament will be retained by the bodily tissue 36 as the needle 33 penetrates the tissue. Retention of the tip 20 while the collar 26 is slid further away from the housing 22 will cause the filament 18 to flex within the tubular extension 16. Retention of the tip 20 will also cause the loop 22 to deform and compress like a spring as shown in FIG. 2. The flexure in the portion of the filament contained in the tubular extension together with the compression of the loop 22 will bring a force to bear on the distal tip 20.

When, as illustrated in FIG. 3, the sharpened end 35 of the needle 33 penetrates the wall of the vessel 37 and enters the cavity space, the distal tip 20 of the filament will no longer be retained and will be moved forwardly beyond the needled end to release the flexure of the filament and the compression of the filament loop 22. Easy detection of this movement can be afforded by deposition of a brilliant, easily-visible area of color 44 on the filament that can be seen through the transparent tubular extension 16. The operator watches for the sudden movement of this area in a direction toward the needle 33, and, upon detecting it, determines that the sharpened end 35 has entered the cavity.

Since the needle penetration indicator 10 permits the determination of cavity penetration to be made virtually simultaneously with entry of the sharpened end of a needle into the cavity, the chances of the end being pushed through the cavity to the wall of tissue on its other side are greatly reduced.

However, to further guard against the sharpened end 35 penetrating the far wall 45 of the vessel 37, the tip 20 bends along the inner surface of the wall 45 as shown in FIG. 3. The flexure of the tip 20 interposes a portion of the filament 18 adjacent the tip 20 between the wall 45 and sharpened end 35. The end 35 is thereby prevented from stabbing through the wall 45.

A further advantageous feature of the needle penetration indicator and guide is that its design also reduces the chances of breaking off the distal tip 20 when the filament 18 is withdrawn from the needle 33 while the sharpened end 35 remains in the penetrated bodily cavity. If the tip 20 should hang up on the needled end before it is withdrawn into the needle tube 34, further backing of the filament 18 by rearward movement of the sliding collar will be taken up by expansion of the rear loop. This is shown in FIG. 4 where the minor chord 48 of the loop is moved by the collar 26 in the direction indicated by the arrow until stopped by the rear end 25a of the housing 16. The major chord 47 of the loop is held in place because of the inability of the distal tip 20 to move past the sharpened end 35. Thus, the filament's capacity for bearing strain is enhanced by the rear loop, and this capacity can be made large enough to prevent breakage of the tip to release the strain before the minor chord 48 is stopped by the rear end 25a of the housing 16. This contributes substantially to the safety of operation of the needle penetration indicator and guide.

To complete the procedure of using the apparatus of the invention, once the vessel 37 is penetrated and the needle fixed with the end 35 in the vessel's interior, the catheter 38 is slid along the needle 33 until it enters the vessel 37. The needle can then be withdrawn with the filament 18 left in the vessel to guide the tip or the catheter therein.

Obviously, many modifications and variations of the needle penetration indicator and guide are possible in light of the above teachings. It is therefore to be understood that within the scope of the claims that follow, the described invention can be practiced other than as specifically described.

I claim:

1. An apparatus for indicating penetration of a needle into a lumen, comprising:
   a hollow needle with a sharpened end: and
   a penetration indicator, including:
      a housing providing a surface to grasp;
      mounting means for mounting said hollow needle to said housing in a position for inserting said sharpened end through body tissue;
      a flexible, resilient filament with a distal tip, movably disposed in said mounting means;
      moving means for, when said hollow needle is mounted to said housing in said position, moving said distal tip through said needle to a position proximate to said sharpened end;
      bias means, acting between said moving means and said filament, for exerting a longitudinal force on said filament, directed toward said distal tip while said tip is prevented from moving through the sharpened end of said needle; and
      means on said filament for indicating when said filament distal tip moves through said sharpened end.

2. The apparatus of claim 1 wherein said mounting means includes a transparent tube and said indicating means includes a visible indication on said filament.

3. The apparatus of claim 1 wherein said mounting means is a hollow tube, said bias means includes a compressible loop movably disposed in said housing, and said filament has an elongate midsection movably disposed in said tube and joining said loop and said distal tip.

4. The apparatus of claim 3 wherein said moving means includes a collar slidably mounted on said tube and attached to said compressible loop for being moved on said tube to induce a flexure in said midsection and compress said loop while said distal tip is prevented from moving through said sharpened end.

5. The apparatus of claim 1 wherein said bias means includes a compressible loop integral with said filament, said loop being compressed when said filament is moved thorugh said needle toward said sharpened end while said distal tip is prevented from moving through the sharpened end, said compression being transmitted through said filament to said distal tip.

6. The apparatus of claim 1 wherein said filament is formed from a coiled stainless steel wire and said distal tip has relatively more flexibility than the rest of said coiled stainless steel wire.

7. An apparatus for providing an indication of insertion of the sharpened tip of a needle into a lumen or other bodily cavity and for preventing transfixation of said bodily cavity by said needle, comprising:
   a hollow needle with an apertured, sharpened end for being inserted through bodily tissue into a cavity;
   a housing providing a surface to hold while inserting said sharpened end;
   mounting means for mounting said needle to said housing in a position for stabbing said sharpened end through bodily tissue;
   a filament with a flexible distal tip, movably disposed in said mounting means;
   moving means movably mounted on said housing for moving said filament through said needle toward said sharpened end;
   biasing means connected to said moving means and to said filament for biasing said distal tip against bodily tissue by exerting a longitudinal force along said filament toward said distal tip in response to said moving means moving said filament toward said sharpened end; and
   means on said filament for indicating when said filament distal tip moves through said sharpened end.

8. The apparatus of claim 7 wherein said mounting means includes a transparent tube and said indicating means includes a visible indication on said filament.

9. The apparatus of claim 7 wherein said mounting means is a hollow tube and said filament has an elongate midsection movably disposed in said tube and said biasing means comprises a compressible loop movably disposed in said housing and joined by said midsection to said distal tip.

10. The apparatus of claim 9 wherein said moving means includes a collar means slidably mounted on said tube and attached to said loop for being moved on said tube to induce a flexure in said midsection and to compress said loop when said distal tip is retained in said needle by bodily tissue.

11. The apparatus of claim 7 wherein said biasing means includes compressible means attached to said filament for being compressively loaded when said filament is moved through said needle toward said sharpened end, said loading being transmitted through said filament to said distal tip while said distal tip contacts bodily tissue through which said sharpened end is being stabbed.

12. The apparatus of claim 7 wherein said filament is formed from a coiled stainless steel wire.

13. The apparatus of claim 7 wherein said distal tip has flexibility sufficient to conform said filament adjacent said tip to an interior surface of a cavity penetrated by said needle for blocking said sharpened end from penetrating said interior surface.

14. A method for indicating when the sharpened end of a hollow needle being inserted into bodily tissue enters a lumen or other bodily cavity by means of an indicator mechanism including a flexible filament with a distal tip and a compressible biasing arrangement connected to said filament, comprising the steps of:
   inserting said flexible filament, distal tip first into a hollow needle having an apertured, sharpened end;
   stabbing the sharpened end of said needle into bodily tissue;
   moving said distal tip of said filament through said needle to said sharpened end;
   operating said biasing arrangement to exert on said filament enough axially-directed force to urge said distal tip against said tissue to be retained thereby within said needle while said stabbing continues;
   indicating when said filament distal tip moves through said sharpened end upon said sharpened end penetrating a space inside said bodily tissue; and
   removing said filament from said needle after said step of indicating.

15. The method of claim 14 further including the steps of slidably mounting a catheter on said needle and sliding said catheter along said needle to penetrate said space after said step of indicating but before said step of removing.

* * * * *